United States Patent [19]

Jess

[11] 4,031,891

[45] June 28, 1977

[54] AIR ELIMINATING FILTER

[75] Inventor: Thurman S. Jess, Mundelein, Ill.

[73] Assignee: Baxter Travenol Laboratories, Inc., Deerfield, Ill.

[22] Filed: Nov. 3, 1975

[21] Appl. No.: 628,435

[52] U.S. Cl. .................. 128/214 R; 128/214.2; 210/308; 210/436
[51] Int. Cl.² ........................................ A01M 5/16
[58] Field of Search ............. 55/159; 210/DIG. 23, 210/308, 316, 441, 436; 128/214 R, 214 C, 214.2

[56] References Cited

UNITED STATES PATENTS

| | | | |
|---|---|---|---|
| 1,547,246 | 7/1925 | Weaver | 210/441 |
| 2,489,966 | 11/1949 | Laure et al. | 128/214 R X |
| 3,631,654 | 1/1972 | Riely et al. | 55/159 |
| 3,803,810 | 4/1974 | Rosenberg | 55/159 |
| 3,854,907 | 12/1974 | Rising | 55/159 |

*Primary Examiner*—Dalton L. Truluck
*Attorney, Agent, or Firm*—Garrettson Ellis; Paul C. Flattery

[57] ABSTRACT

An air eliminating filter for use in filtering intravenous or other liquids including an elongate hollow tubular member provided with inlet means at one end and having at least two window openings spaced longitudinally thereon, a hydrophilic filter element capable of passing liquid therethrough when the filter element has been wetted with liquid while simultaneously blocking air interposed in one of the window openings, at least one hydrophobic filter element capable of repelling liquid and passing air therethrough positioned in the other of the window openings and communicating with the ambient air and manifold means including outlet means to discharge liquid therefrom mounted on the tubular member communicating with the hydrophilic filter whereby the hydrophilic filter is wetted with liquid passed into the tubular member through the inlet means to permit the hydrophilic filter to pass liquid therethrough while simultaneously blocking air. The liquid passing through the hydrophilic filter element is collected in the manifold means for discharge through the outlet means while air in the tubular member is discharged through the hydrophobic filter.

2 Claims, 6 Drawing Figures

U.S. Patent June 28, 1977 Sheet 1 of 3 4,031,891
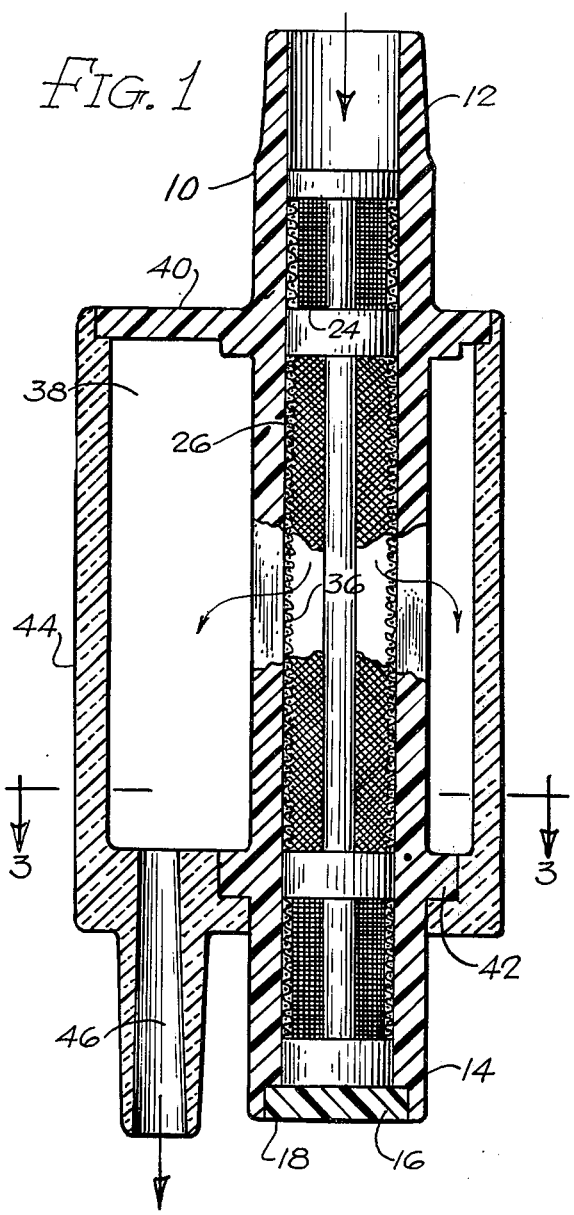
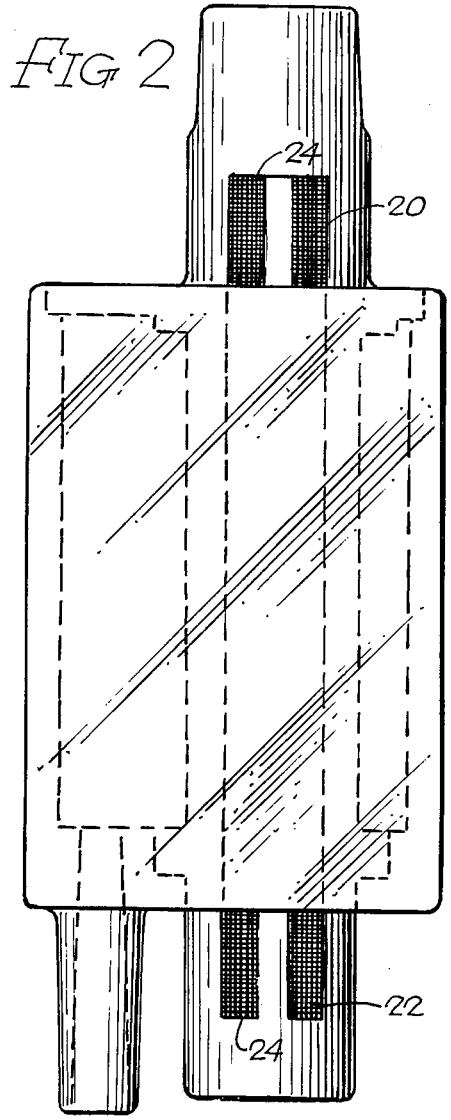
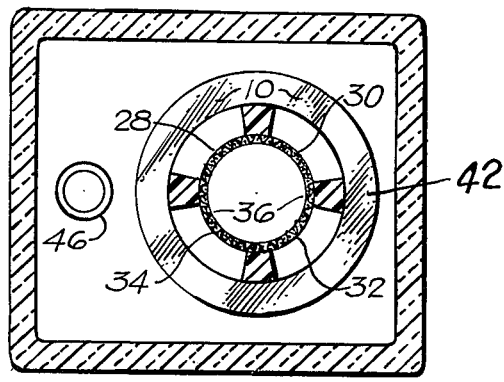

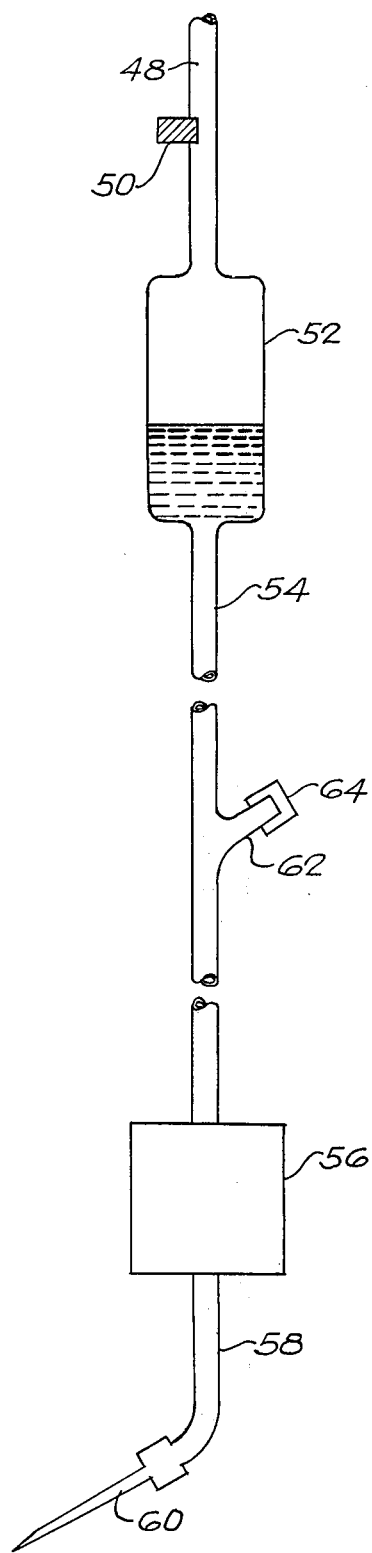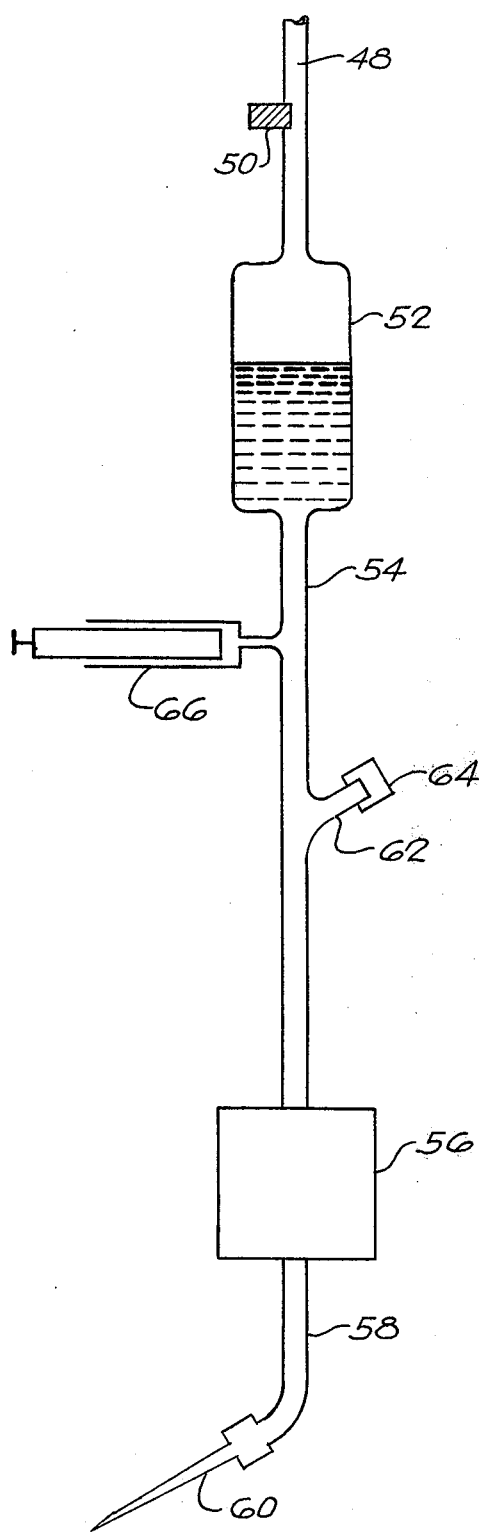

AIR ELIMINATING FILTER

This invention relates to systems for administration of intravenous solutions, and more particularly to filters for use in such systems.

In the administration of intravenous solutions, it is frequently desirable to filter such solutions just prior to their infusion into a patient to remove any solid particulate matter including bacteria, undissolved solids and the like. In recent years, increasing use has been made of what have become known in the art as hydrophilic filters in which there is employed a filter element having hydrophilic filter characteristics whereby the hydrophilic filter, when wetted with liquid, is capable of passing liquid through the pores thereof while simultaneously blocking air or like gases. The use of such hydrophilic filter elements is therefore highly desirable because they prevent the infusion of air into the patient provided that the filter element has been wetted with the liquid.

One filter embodying a hydrophilic filter element is described in U.S. Pat. No. 3,471,019. The filter described in that patent functions satisfactorily except when, in certain positions, an air bubble present in the filter housing can spread over the surface of the hydrophilic filter to thereby effectively cut off any further liquid flow through the filter. Care must be taken, therefore, in using such a filter that it is not positioned in such a way that the hydrophilic filter element can be rendered impermeable to liquid flow.

It has also been proposed to render such air blocking filters air eliminating to provide a convenient method for the discharge of air from the filter housing. One effort to produce an air eliminating filter which is position insensitive is described in U.S. Pat. No. 3,523,408. There is shown in that patent a filter said to be position insensitive; position insensitivity is provided by spacing the hydrophobic and hydrophilic filter elements together, as by a distance of 0.5 to 2 mm to insure that gas bubbles formed between the two filter elements do not result in blockage of the liquid flow through the hydrophilic filter element. The necessity for the close spacing in that device represents a distinct disadvantage because it necessarily depends on maintaining relatively precise tolerances. The design also requires use of a hydrophobic filter element sufficiently large to match or overlap the entire surface of the hydrophilic filter element, adding to the cost of such an assembly.

It is accordingly an object of the present invention to provide a filter for use in the administration of intravenous solutions which overcomes the foregoing disadvantages.

It is a more specific object of the invention to provide a filter for use in the administration of intravenous solutions which is air blocking and air eliminating.

It is a further object of the present invention to provide an air blocking and air eliminating filter for use in the administration of intravenous solutions which is capable of providing high fluid flow and which is position insensitive whereby relatively large amounts of air in the filter do not interrupt liquid flow, regardless of the position of the filter.

It is yet another object of the present invention to provide intravenous administration sets embodying the filter of this invention.

These and other objects and advantages of the invention will appear more fully hereinafter, and for purposes of illustration, but not of limitation, an embodiment of the invention is shown in the accompanying drawing wherein:

FIG. 1 is an exposed top view of a filter embodying the concepts of this invention;

FIG. 2 is a top view of the filter illustrated in FIGURE 1;

FIG. 3 is a sectional view taken along the lines 3—3 in FIG. 1;

FIG. 4 is a schematic view of an intravenous administration set embodying the filter of this invention; and FIG. 5 is a schematic view of an alternative intravenous administration set embodying the filter of the invention.

Figure 3A:
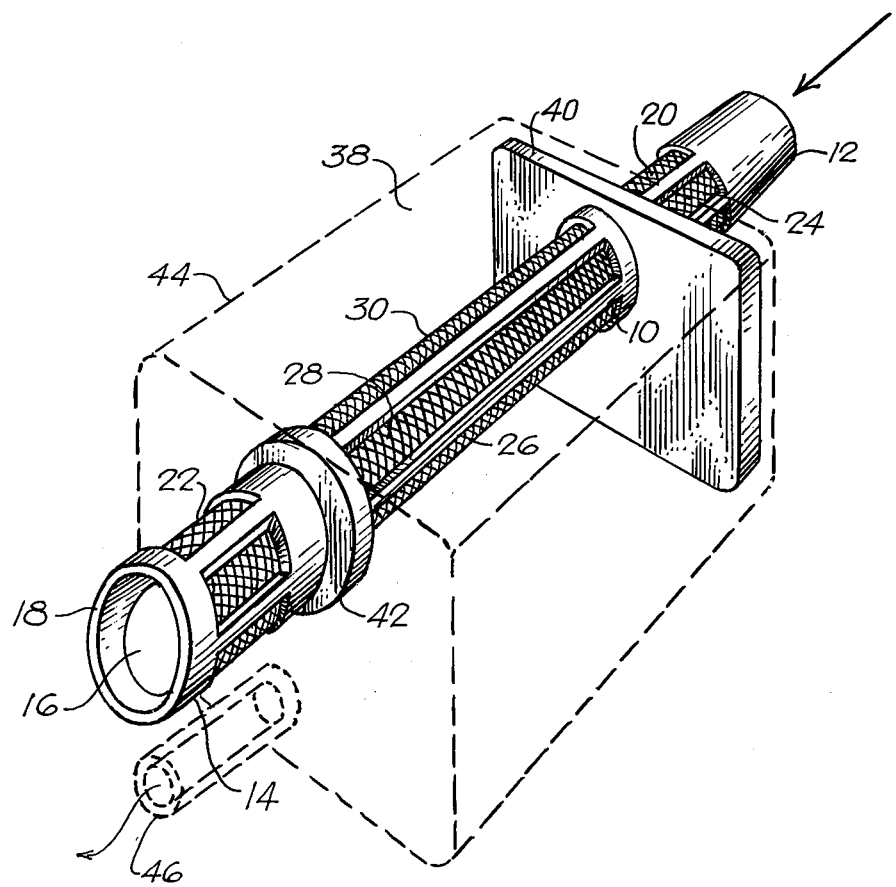
FIG. 3A is a perspective view of the filter illustrated in FIGS. 1–3.

The concepts of the present invention reside in an air blocking and air eliminating filter for use in the intravenous administration of liquids which is position insensitive, that is, capable of passing liquid through a hydrophilic filter element for discharge from the filter no matter how the filter is disposed provided that the hydrophilic filter has been wetted with a liquid. The filter of this invention is also air eliminating in that it includes at least one hydrophobic filter element which is capable of repelling liquid and permitting the passage of air in the filter through the hydrophobic filter element to the ambient atmosphere to eliminate air from the system. The filter of this invention is capable of accommodating high fluid flows and can be easily and inexpensively manufactured by readily available molding techniques.

In accordance with the practice of this invention, the filter includes an elongate hollow tubular member provided with inlet means at one end and having at least two window openings spaced longitudinally along it. Positioned in and covering one of the window openings is a hydrophilic filter element which is capable of passing liquid therethrough when the hydrophilic filter element is wetted with liquid while simultaneously blocking the passage of air or other gases therethrough. Positioned in and covering the other window opening is a hydrophobic filter element which is capable of repelling liquid and passing air therethrough. The hydrophobic filter element communicates with the ambient atmosphere and thus provides means to eliminate air contained within the tubular member for elimination from the system.

The hydrophilic filter element, on the other hand, communicates with manifold means mounted on the tubular member and communicating therewith. In this way, liquid to be filtered is introduced to the tubular member and passes into it where it wets the hydrophilic filter element. Once wetted with liquid, the hydrophilic filter element permits the passage of liquid therethrough while simultaneously blocking air whereby the liquid passed through the hydrophilic filter element enters the manifold means and is discharged from the manifold means through outlet means provided therein. As indicated, any air entering the hollow tubular member is eliminated from the system through the hydrophobic filter element.

Referring now to the drawings for a more detailed description of the invention, there is shown in FIG. 1 a top view which is exposed to illustrate the details as to the filter of this invention. The filter includes an elongate hollow tubular member designated as 10 which is provided at one end with inlet means 12. In the peferred practice of this invention, the tubular member 10 is open at its opposite end 14, but is provided with a plug 16 positioned in the opening 18 to thereby prevent fluid flow through the end 14 opposite the inlet means 12.

The tubular member 10 includes at least one, and preferably two, window openings 20 and 22 extending through the walls of the tubular member 10 and thereby communicating with the ambient atmosphere. These window openings are shown most clearly in FIG. 2 of the drawing, with window opening 20 being positioned adjacent to the inlet means 12 and window opening 22 being positioned adjacent to the opposite end 14. While the window openings 20 and 22 are illustrated in the drawing as a single opening in the periphery of the tubular member 10, it is sometimes desirable to provide the window openings 20 and/or 22 in a plurality of sections extending radially about the periphery of the tubular member 10. Thus, for example, there can be provided a window opening diametrically opposite the window opening 20 shown in FIG. 2.

Positioned in and covering each of the window openings 20 and 22 is a hydrophobic filter element 24 as illustrated in FIG. 2 of the drawing. When the window openings 20 and 22 are formed in a plurality of sections about the periphery of the tubular member 10, then it is desirable to employ, as the hydrophobic filter element, an annular filter element dimensioned to correspond to the internal diameter of the tubular member 10 whereby the annular hydrophobic filter element 24' as illustrated in FIG. 1 of the drawing can simply be inserted into and bonded or molded to the tubular member 10 to overlay all sections of the window openings 20 and/or 22.

The tubular member 10 is provided with a central window opening generally designated as 26 in FIG. 2. That window opening is preferably formed of a plurality of sections designated 28, 30, 32 and 34 as illustrated in FIG. 3 of the drawing, with the various window openings 28, 30, 32 and 34 being radially spaced about the periphery of the tubular member 10. Each section 28, 30, 32 and 34 of the window opening 26 is provided with a hydrophilic filter element generally designated as 36. In the preferred practice of the invention as shown in FIGS. 1 and 3, the hydrophilic filter element is in the form of an annulus dimensioned to correspond to the internal diameter of the tubular member 10 whereby the annulus 36 can be inserted into the tubular member 10 to overlie each of the sections 28, 30, 32 and 34 of the window opening 26. In this way, each section of the window opening 26 is provided with a hydrophilic filter element.

Hydrophilic filter elements for use in the practice of this invention are, of themselves, known to those skilled in the art and form no part of the present invention. Such hydrophilic filter elements are described in detail in the foregoing patents and generally have a pore size ranging between 0.1 μm to 14 μm. Similarly, hydrophobic filter elements for use in the practice of this invention are likewise well known to those skilled in the art.

Surrounding the central window opening 26 and its sections 28, 30, 32 and 34 is manifold means defining a chamber 38 communicating with the sections 28, 30, 32 and 38 of the central window opening 26. The manifold 38 is defined by flange members 40 extending radially from the tubular member 10 and mounted thereon to define one wall of the manifold 38. Also provided is a flange 42 spaced longitudinally from the flange 40 and mounted on the tubular member 10. The lateral walls of the manifold 38 are defined by a panel generally designated as 44 which is adapted to engage flanges 40 and 42 in a sealing relationship. For example, the lateral panel 44 can simply be bonded as by any conventional means to the flanges 40 and 42 to thereby define the manifold chamber 38. As is shown in FIG. 1 of the drawing, the lateral panel 44 also defines outlet means 46, with the outlet means 46 communicating with the manifold 38.

As will be appreciated by those skilled in the art, the configuration of the manifold 38 can be widely varied. Also, the manifold 38 can have a rectangular cross section as shown in FIG. 3 of the drawing or the cross section can be circular or any other polygonal shape.

In use, the intravenous liquid to be infused into the patient is introduced to the tubular member through the inlet means 12 and enters the interior of the tubular member 10. Since the tubular member is closed at its opposite end 14, the liquid entering the tubular member 10 accumulates therein and serves to wet the hydrophilic filter element 36 covering the central window opening 26. Once wetted with liquid, the hydrophilic filter element 36 becomes permeable to liquid (but simultaneously impermeable to air or like gases) to permit the liquid to pass through the hydrophilic filter element 36 and through one or more of the sections 28, 30, 32 or 34 of the central window opening 36 into the manifold 38 for discharge through the outlet means 46. At the same time, any air which may be present in the tubular member 10 is blocked by passage through the wet hydrophilic filter element 36. It can pass through the hydrophobic filter element 24 for elimination from the system since those filter elements have not been wetted with liquid due to their hydrophobic characteristics.

The filter of this invention is position insensitive because no matter how the tubular member 10 is disposed, liquid entering therein comes into contact with the hydrophilic filter element 36 to wet the filter element since the hydrophilic filter element is in the form of a sleeve covering the entire internal periphery of the tubular member 10 adjacent to the central opening 26. If only a small amount of liquid is in the tubular member 10, that liquid accumulates in the interior of the tubular member 10 to contact at least a portion of the hydrophilic filter element 36.

While the invention has been described above as using three different filter elements, namely a hydrophilic filter element to cover the central window opening 26 and separate hydrophobic filter elements covering the opposing window openings 20 and 22, it will be understood by those skilled in the art that use can also be made of a continuous sleeve of filter material, the ends of which have been rendered hydrophobic in nature and the central portion of which has been rendered hydrophilic in nature. In using a filter element of this type, a single sleeve can be inserted into and bonded or molded to the tubular member 10 whereby the hydrophobic portions thereof cover the window openings 20 and 22 while the hydrophilic portions thereof cover the central window opening 26 including all sections thereof including 28, 30, 32 and 34.

The filters of the present invention are ideally suited for use in the filtration of intravenous solutions, blood or other liquids infused to patients where filtration just prior to administration is desired. They can be used in combination with intravenous administration sets of the type illustrated in FIG. 4 of the drawing. As shown in that figure, the set includes a hollow male connector 48 adapted to be connected to a source of intravenous liquid (not illustrated in the drawing). To secure the connector 48 to the source of the liquid, the connector 48 is provided with a finger grip flange 50. The connector 48 thus communicates with a drip chamber 52 into which the intravenous liquid is allowed to pass. From the drip chamber 52, the intravenous liquid passes through tubing means 54 to the filter 56 of the type illustrated in FIGS. 1-3 of the drawing. Liquid effluent from the outlet means 46 from the filter passes therefrom to a third tubing 58 to the patient by way of an appropriate needle or like administration means 60 communicating therewith.

It is frequently desirable that the intravenous administration set include an injection site for the purpose of enabling medical preparations to be added to the system independent of the liquid supplied to the drip chamber. For this purpose, one of the tubing means, and preferably the tubing means upstream of the filter 56 is provided with a "Y" injection site formed of a branch tubing means 54 and having an elastomeric injection plug 64 through which a medical preparation can be injected by way of a hypodermic syringe.

In many instances of intravenous administration, it is desirable to employ pump means to control and/or facilitate the delivery of the intravenous liquid to the patient. One such administration system is illustrated in FIG. 5 of the drawing. In this embodiment, the administration set if generally the same as that shown in FIG. 4 except that the conduit means 54 between the drip chamber 52 and the filter 56 includes pump means generally designated as 66. In the embodiment illustrated in FIG. 5, the pump means 66 is schematically shown as a syringe pump, the details of which are well known to those skilled in the art. As will also be appreciated by those skilled in the art, the syringe may be mechanically driven, or alternatively, may be replaced by any of a variety of conventional mechanical pumps commercially available for pumping intravenous solutions.

In each of the administration sets illustrated in FIGS. 4 and 5 of the drawing, the filter 56 embodying the features of this invention serves to filter the intravenous solution while preventing any accidental infusion of ar into the patient.

It will be understood that various changes and modifications can be made in the details of construction, procedure and use without departing from the spirit of the invention, espcially as defined in the following claims.

I claim:

1. An air-eliminating filter for intravenous liquids comprising:

an elongated, hollow, tubular filter support member defining inlet means at one end thereof and closed at its other end, a plurality of circumferentially-spaced, longitudinally extending ribs defined along an intermediate portion of said tubular member, and circumferentially spaced window portions defined between said ribs to permit communication between the interior and exterior of said tubular support member;

a tubular, hydrophilic filter element capable of passing aqueous liquid therethrough when wet with said liquid, while simultaneously blocking the flow of air, positioned wthin said tubular member in coaxial relationship thereto, said hydrophilic filter element being carried by a central portion of said ribs to occlude central portions of said window openings;

a pair of tubular, hydrophobic filter elements capable of repelling aqueous liquid and passing air therethrough, each being positioned adjacent an end of said hydrophilic tubular filter element, said hydrophobic filter elements being carried by end portions of said ribs to block flow through end portions of said window openings, and manifold means mounted on said tubular member to enclose said hydrophilic filter but not to enclose said hydrophobic filters, said manifold means including outlet means to discharge liquid therefrom.

2. An administration set for parenteral solutions comprising a flexible, tubular conduit, said conduit including separate sections communicating respectively with the inlet and the outlet of the filter of claim 1.

* * * * *